United States Patent [19]

Mason et al.

[11] Patent Number: 4,804,792

[45] Date of Patent: Feb. 14, 1989

[54] NITRATION OF BENZENE OR TOLUENE IN A MOLTEN NITRATE SALT

[75] Inventors: Robert W. Mason, Lake Charles; R. K. Steely, Sulphur, both of La.

[73] Assignee: Olin Corporation, Cheshire, Conn.

[21] Appl. No.: 149,258

[22] Filed: Jan. 28, 1988

[51] Int. Cl.$^4$ ............................................. C07C 79/10
[52] U.S. Cl. .................................... 568/939; 568/940; 568/927
[58] Field of Search ............... 568/937, 938, 939, 927, 568/940

[56] References Cited

U.S. PATENT DOCUMENTS

| | | |
|---|---|---|
| 2,905,724 | 9/1959 | Martin ................................. 260/644 |
| 3,715,323 | 2/1973 | Crivello . |
| 4,064,147 | 12/1977 | Thelen et al. . |
| 4,310,500 | 1/1982 | Langecker et al. ............. 568/939 X |
| 4,618,733 | 10/1986 | Schumacher ...................... 568/927 |
| 4,621,157 | 11/1986 | McDaniel . |

*Primary Examiner*—John F. Terapane
*Assistant Examiner*—Susan Wolffe
*Attorney, Agent, or Firm*—Dale Lynn Carlson

[57] ABSTRACT

Nitration of benzene or toluene, and more specifically to such a reaction in a molten nitrate salt medium.

11 Claims, No Drawings

NITRATION OF BENZENE OR TOLUENE IN A MOLTEN NITRATE SALT

FIELD OF THE INVENTION

This invention relates generally to the nitration of benzene or toluene, and more specifically to such a reaction in a molten nitrate salt medium.

BACKGROUND OF THE INVENTION

The vapor phase nitration of benzene and toluene, and halogenated derivatives thereof, is known in the art. By way of illustration, U.S. Pat. No. 4,618,733 discloses the vapor phase nitration of aromatic compounds, notably chlorobenzene, with nitric acid in the presence of metal oxide catalyst and a sulfur trioxide catalyst. This patent discloses at column 7, lines 48-53 the use of eutectic salt baths as a medium to maintain the reactor surfaces at a relatively constant temperature and to conduct heat from the reactor. The reaction time disclosed in this patent for the illustrated batch reactions is long, typically between 3 and 7 hours. Moreover, the equipment and the catalyst requirements for this system are relatively more complex than might be desired.

New, simpler nitration methods for nitrating aromatic hydrocarbons, preferably with fast reaction times, would be highly desirable in the industry.

SUMMARY OF THE INVENTION

The present invention relates to a method of nitrating an aromatic hydrocarbon selected from the group consisting of benzene, and toluene, which comprises contacting said aromatic hydrocarbon with concentrated nitric acid in the presence of a molten nitrate salt selected from the group consisting of the nitrate salts of sodium, potassium, lithium, and mixtures thereof, in a vapor phase reaction at a reaction temperature of between about 150° C. and about 250° C. and a reaction pressure of between about 100 mm of Hg and one atmosphere and for a reaction time not exceeding one hour to produce a product containing nitrobenzene or nitrotoluene.

DETAILED DESCRIPTION OF THE INVENTION

In accordance with the present invention, it has now been surprisingly found that the nitration of benzene or toluene is suitably effected in a facile manner by reaction with concentrated nitric acid in the presence of a select molten nitrate salt(s) under specific pressure and temperature reaction conditions.

The reaction temperature is suitably maintained by the molten salt at between about 150° C. and about 250° C. during the reaction in accordance with the present invention. The specific molten salt(s) selected is based on the melting point thereof at the desired reaction temperature. At temperatures of the upper end of this temperature range, mixtures of potassium nitrate and sodium nitrate are preferred, whereas at the lower end of this temperature range eutectic mixtures of potassium nitrate, sodium nitrate, and lithium nitrate are preferred.

A particularly preferred molten salt mixture is a mixture of potassium and sodium molten nitrate salts containing between about 20 and about 80 weight percent of sodium nitrate, more preferably between about 45 and about 65 weight percent of sodium nitrate based upon the total amount of sodium nitrate and potassium nitrate in the molten salt mixture. Another particularly preferred molten salt mixture is a mixture of sodium, potassium, and lithium nitrate containing between about 10 and about 30 weight percent of lithium nitrate and between about 15 and about 75 weight percent of sodium nitrate based on the total amount of the mixture.

It is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" nitration reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The molten salt(s) serves as a temperature regulator for the reaction and as an isothermal medium for the reactants. More specifically, the molten nitrate salt(s) have a high heat absorption capacity, enabling them to absorb large quantities of heat during the exothermic nitrate reaction while maintaining an essentially constant reaction temperature and thereby preventing a runaway reaction. The absorbed heat of reaction from this exothermic nitrate reaction may be employed in the process of the present invention to help maintain the molten salt in a molten state and/or to heat the gaseous reactants to reaction temperature, absorbing the reaction exotherm. Typically, the molten salt(s) is employed in an amount on a weight basis of between about 5 times and about 100 times (preferably between about 5 times and about 50 times) the total weight of the reactants employed.

A preferred method of contacting the reactants in the presence of the molten nitrate salt is by bubbling the reactants into a bath of the molten salt by means of a carrier gas such as nitrogen. If the reactants are bubbled into the bottom of the bath or column containing the molten nitrate salt, the contact time of the reactants with the molten salt catalyst is equal to the "rise time" of the reactants through the bath or column.

Thus, the contact time can be increased by increasing the length of the molten nitrate salt bath or column. An alternate method of contacting the reactants in the presence of the molten salt would be to pass the reactants through a reactor countercurrently to a spray or mist of the molten salt. This latter method provides for enhanced surface area contact of the reactants with the molten salt. Still another method of contacting the reactants with molten salt would be to inject the reactants into a circulating stream of molten salt, wherein the kinetic energy of both streams is utilized to provide intimate mixing through the application of nozzles, mixers, and other conventional equipment. These methods are only illustrative of types of reaction systems which may be employed in the practice of this disclosure. Other conventional methods of gas-liquid contact in reaction systems may also be employed.

The benzene or toluene feed can be passed into the molten nitrate salt-containing reactor using a separate stream (e.g., feed tube) from the stream delivering the concentrated nitric acid to the reactor. Alternatively, the reactant gases can be fed into the reactor together in a single stream. In a preferred embodiment of the present invention, two feed tubes are employed. Mixing of the reactants prior to, or at the point of, the inlet into the reactor is desired in order to facilitate the nitration reaction. Mixing is suitably accomplished using an impingement mixer or sparger tube.

The concentrated nitric acid useful in the present invention typically has a concentration of between about 50 percent and about 90 percent by weight of acid based on the weight of water plus acid contained therein, preferably between about 90 percent and about 99 percent by weight of acid.

A catalyst is not required for the method of the present invention. However, if a catalyst is used, the molten salt(s) will act as an isothermal medium for it to prevent, for example, overheating of the catalyst.

This process can be run in a batchwise or continuous operation, the latter being preferred. The order of introduction of the reactants is determined by the operator based on what is most safe and practical under prevalent conditions. Generally, the desirability of avoiding flammable or explosive mixtures throughout the reaction and subsequent product separation systems will dictate the desired procedures.

The process can be carried out by feeding a mixture of benzene or toluene, inert carrier gas, and concentrated nitric acid into a reaction vessel containing molten nitrate salt. The molar ratio of nitric acid to aromatic compound is preferably between about 0.1: and about 15:1, more preferably between about 0.3:1 and about 12.5: respectively. The lower ratios are preferred for mononitration and to minimize by-product formation. Typically, desired nitrated products include mononitrobenzene or dinitrotoluene. The reaction vessel is typically made of glass, glass-lined metal, or titanium. For example, a glass-lined stainless steel autoclave can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt products, or to extend the useful life of the reaction system.

Some form of agitation of the molten salt(s)/feed mixture is preferred to avoid a static system and insure the homogeneity of the molten salt. Agitation helps prevent crust formation of the salt(s) at the head gas/salt interface in the reactor. This can be accomplished by using a mechanically stirred autoclave, a multi-point injection system, or a continuous process, e.g., with a loop reactor wherein the reactants are force circulated through the system.

The process of the present invention is suitably carried out at atmospheric or subatmospheric pressure. Preferably, the process is effected at atmospheric pressure, since this pressure minimizes equipment requirements. Reaction times of less than 60 seconds are typical. To prevent internal refluxing of reactants, which increases reaction times, subatmospheric pressures can be used when reacting higher molecular weight, higher boiling point substrates, particularly when it is desired to perform the reaction at low reaction temperatures.

It is to be understood that by-products are also produced during the reaction. For example, some oxidation of the feed is also effected, particularly at high temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation. The following examples are intended to illustrate, but in no way limit the scope of, the present invention.

EXAMPLE 1

Benzene Nitration at 150° C. and Atmospheric Pressure Using a Molten Sodium Nitrate/Potassium Nitrate/Lithium Nitrate Salt Bath A two inch diameter by 18 inch length of stainless steel pipe, sealed on the bottom and flanged on the top, was equipped with two full length ⅛ inch diameter Hastelloy C diptubes, a thermocouple and magnetic stir bar stripped of its Teflon coating. The reactor was charged with 81.6 g of sodium nitrate, 327.7 g of potassium nitrate and 124.2 g of lithium nitrate and the salts melted by electrical resistance heating of the reactor shell. The molten salt mixture was gently sparged with dry nitrogen gas, venting the reactor to the atmosphere through an ice water and Dry Ice/isopropanol product collection system. The molten salt temperature was adjusted to 150° C. and 50 cc/minute nitrogen fed to each diptube. Benzene (20 ml, 17.6 g, 0.22 mole) was fed to one diptube and 98 percent nitric acid (6 ml, 9.02 g, 0.14 mole) fed to the other. Feed rates were 0.38 ml benzene/minute and 0.13 ml nitric acid/minute, set by the Sage Instruments syringe pump used to meter in the reactants. Upon completion of reactant addition, the reactor system was flushed with nitrogen for an additional 15 minutes. The ice water product trap contained 23.59 g of a red, 2-phase liquid. Separation of the layers furnished 3.35 g of nitric acid. The organic layer was washed with saturated sodium chloride solution, dried over magnesium sulfate and filtered to give 17.5 g of liquid, analyzing as 78.3 percent benzene and 21.7 percent nitrobenzene (0.031 mole). Approximately 41 percent of the nitric acid equivalent fed to the reactor was thus vented from the product collection system as $NO_x$ vapors, while aromatic recovery was 94 percent.

EXAMPLE 2

Benzene Nitration at 200oC and Atmospheric Pressure Using a Molten Sodium Nitrate/Potassium Nitrate/Lithium Nitrate Salt Bath Using the apparatus described in EXAMPLE 1, 50 ml nitrogen/minute was sparged through each feed line into the molten salt, heated to 200° C. To one feed line was added 9 ml of benzene at 0.19 ml/minute, with 6 ml of 98 percent nitric acid added to the other feed line at 0.13 ml/minute. A total of 12.17 g of red, 2-phase liquid product was collected in the ice water trap. Separation of the layers gave 9.35 g of organic material. The organic layer was washed with 10 ml of water, dried over magnesium sulfate, filtered and analyzed as 66.86 percent benzene and 33.14 percent nitrobenzene.

EXAMPLE 3

Benzene Nitration at 250° C. and Atmospheric Pressure Using a Molten Sodium Nitrate/Potassium Nitrate Salt Mixture Using the apparatus described in EXAMPLE 1, but substituting 351 g of sodium nitrate and 234 g of potassium nitrate (60:40) for the sodium/potassium/lithium nitrate mixture of EXAMPLE 1, 20 ml of air per minute was sparged through each feed line into the molten salt, heated at 250° C. To one feed line was added 9 ml of benzene, fed at 0.15 ml/minute, with 45 ml of 70 percent nitric acid added to the other feed line at 0.77 ml/minute. The orange 2-phase product collected in the ice water trap was diluted with 50 ml of saturated sodium chloride solution and extracted with 2 × 10 ml of methylene chloride. The combined organic fractions were dried over magnesium sulfate, filtered, and analyzed as 71.92 percent benzene and 28.08 percent nitrobenzene.

EXAMPLE 4

Toluene Nitration at 225° C. and Atmospheric Pressure Using a Molten Sodium Nitrate/Potassium Nitrate/Lithium Nitrate Salt Bath Using the apparatus described in EXAMPLE 1, 95 ml nitrogen/min was sparged through each feed line into the molten salt, heated at 225° C. To one feed line was added 10 ml of toluene (8.67 g) at 0.20 ml/minute, with 21.4 ml of 70 percent nitric acid (30.22 g) added to the other feed line at 0.40 ml/minute. A total of 28.13 g of 2-phase liquid product was collected in the ice water trap. Separation of the layers gave 7.75 g of organic product. The aqueous layer was extracted once with 50 ml of methylene chloride, then the organic layers combined, dried over magnesium sulfate and filtered. The product analyzed as 60.87 percent toluene, 0.11 percent benzaldehyde, 21.35 percent 2-nitrotoluene, 2.19 percent 3-nitrotoluene and 15.09 percent 4-nitrotoluene.

What is claimed is:

1. A method of nitrating an aromatic compound selected from the group consisting of benzene and toluene by a vapor phase reaction of gaseous reactants in contact with a molten nitrate salt selected from the group consisting of the molten nitrate salts of sodium, potassium, lithium, and mixtures thereof, said gaseous reactants being said aromatic compound and concentrated nitric acid, said reaction being carried out at a reaction temperature of between about 150° C. and about 250° C. and a reaction pressure of between about 100 mm of Hg and about one atmosphere, for a reaction time not exceeding one hour, thereby producing nitrobenzene or nitrotoluene.

2. The method of claim 1 wherein the molar ratio of said nitric acid to said aromatic compound is between about 0.1 to 1 and about 15 to 1.

3. The method of claim 1 wherein the molar ratio of said nitric acid to said aromatic compound is between about 0.3 to 1 and about 12.5 to 1.

4. The method of claim 1 wherein said molten salt is employed in a total amount on a weight basis of between about 5 times and about 100 times the total weight of said aromatic hydrocarbon plus said concentrated nitric acid.

5. The method of claim 1 wherein said molten salt is employed in a total amount on a weight basis of between about 5 times and about 50 times the total weight of said aromatic hydrocarbon plus said concentrated nitric acid.

6. The method of claim 1 wherein said molten salt is a mixture of sodium nitrate and potassium nitrate containing between about 20 and about 80 weight percent of sodium nitrate based upon the total amount of said sodium nitrate plus potassium nitrate.

7. The method of claim 1 wherein said molten salt is a mixture of sodium nitrate and potassium nitrate containing between about 45 and about 65 weight percent of sodium nitrate based upon the total amount of said sodium nitrate plus potassium nitrate.

8. The method of claim 1 wherein said molten salt is a mixture of sodium nitrate, potassium nitrate and lithium nitrate containing between about 10 and about 30 weight percent of lithium nitrate and between about 15 and about 75 weight percent of sodium nitrate based on the total amount of said mixture.

9. The method of claim 1 wherein the reaction time is less than 60 seconds.

10. A method of nitrating an aromatic compound selected from the group consisting of benzene and toluene by a vapor phase reaction of gaseous reactants in contact with a molten nitrate salt mixture, said molten nitrate salt mixture being a mixture of potassium and sodium nitrate in an amount of between about 45 and about 65 weight percent of sodium nitrate based upon the total amount of sodium and potassium nitrate in the mixture, said gaseous reactants being said aromatic compound and concentrated nitric acid in a molar ratio of nitric acid to aromatic compound of between about 0.3:1 and about 12.5:1, said reaction being carried out at a reaction temperature of between about 150° C. and about 250° C. and a reaction pressure of between about 100 mm of Hg and about one atmosphere, for a reaction time not exceeding one hour, thereby producing nitrobenzene or nitrotoluene.

11. A method of nitrating an aromatic compound selected from the group consisting of benzene and toluene by a vapor phase reaction of gaseous reactants in contact with a molten nitrate salt mixture, said molten nitrate salt mixture being a mixture of sodium, potassium and lithium nitrates, wherein the lithium nitrate is present in an amount of between about 10 and about 30 weight percent and wherein the sodium nitrate is present in an amount of between about 15 and about 75 weight percent, said weight percents being based upon the total weight of said mixture, said gaseous reactants consisting of said aromatic compound and concentrated nitric acid in a molar ratio of nitric acid to aromatic compound of between about 0.3:1 and about 12.5:1, said reaction being carried out at a reaction temperature of between about 150° C. and about 250° C. and a reaction pressure of between about 100 mm of Hg and about one atmosphere, for a reaction time not exceeding one hour, thereby producing nitrobenzene or nitrotoluene.

* * * * *